(12) United States Patent
Haynes et al.

(10) Patent No.: US 6,544,747 B2
(45) Date of Patent: Apr. 8, 2003

(54) ASSAY SYSTEM

(75) Inventors: Barton F. Haynes, Durham, NC (US); Gregory D. Sempowski, Durham, NC (US); Hua-Xin Liao, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/973,959

(22) Filed: Oct. 11, 2001

(65) Prior Publication Data

US 2002/0068297 A1 Jun. 6, 2002

Related U.S. Application Data

(60) Provisional application No. 60/239,092, filed on Oct. 11, 2000.

(51) Int. Cl.[7] .............................. C12Q 1/68; C12P 73/34
(52) U.S. Cl. ........................ 435/6; 435/91.1; 435/91.2
(58) Field of Search .......................... 435/6, 91.1, 91.2

(56) References Cited

PUBLICATIONS

Al–Harthi et al., "Detection of T cell receptor circles (TRECs) as biomarkers for de novo T cell synthesis using a quantitative polymerase chain reaction–enzyme linked immunosorbent assay (PCT–ELISA)", Journal of Immunological Methods 237: 187–197 (2000).

Sodora et al, "Quantification of thymic function by measuring T cell receptor excision circles within peripheral blood and lymphoid tissues in monkeys", Eur. J. Immunol. 30:1145–1153 (2000).

Douek et al., "Changes in thymic function with age and during the treatment of HIV infection", Nature 396:690–695 (1988).

Sempowski et al., "T Cell Receptor Excision Circle Assessment of Thymopoiesis in Aging Mice", Mol. Immunol. 38:841 (2001).

*Primary Examiner*—Jezia Riley
(74) *Attorney, Agent, or Firm*—Nixon & Vanderhye PC

(57) ABSTRACT

The present invention relates, in general, to an assay system and, in particular, to a molecular assay system for the detection and/or quantification of mouse T cell receptor excision circles. The present system can be used to detect newly produced naïve T lymphocytes and to monitor thymic output and T lymphocyte immune reconstitution in mice.

8 Claims, 3 Drawing Sheets

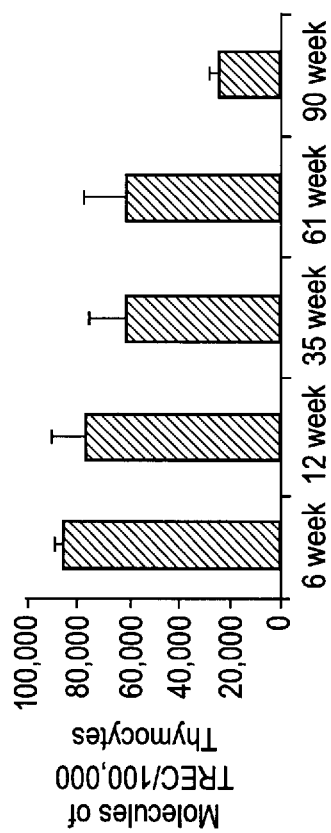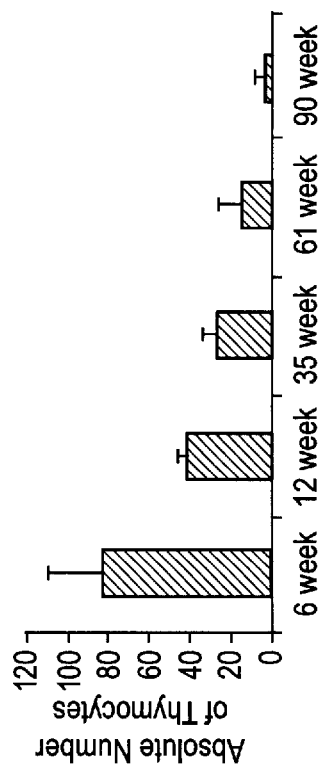

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Probe

<400> SEQUENCE: 1
cattgccttt gaaccaagct g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 2
ttatgcacag ggtgcaggtg                                                20

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Probe

<400> SEQUENCE: 3
cagggcaggt ttttgtaaag gtgctgctca ctt                                 33

ASSAY SYSTEM

This application claims the benefit of provisional application No. 60/239,092, filed Oct. 11, 2000.

TECHNICAL FIELD

The present invention relates, in general, to an assay system and, in particular, to a molecular assay system for the detection and/or quantification of mouse T cell receptor excision circles. The present system can be used to detect newly produced naïve T lymphocytes.

BACKGROUND

T cell receptor excision circles (TRECS) are episomal DNA circles that are generated by the DNA recombination process that is used by T lymphocytes to produce antigen-specific T cell receptors. The non-replicated DNA circles are diluted out with cell division. The present invention provides a method of assaying for newly generated mouse naïve T lymphocytes based on the detection of signal joint TRECs.

SUMMARY OF THE INVENTION

The present invention relates generally to a molecular assay system for the detection and/or quantification of mouse T cell receptor excision circles. More particularly, the invention relates to a method of assaying for newly produced mouse naïve T lymphocytes.

Objects and advantages of the present invention will be clear from the description that follows.

BRIEF DESCRIPTION OF THE DRAWINGS

(FIG. 1A) Real-time quantitative-PCR assay for mouse sjTRECs. Plasmid DNA containing mouse sjTREC DNA sequence is serially diluted to establish a standard curve of molecules of sjTREC. (FIG. 1B) Representative mouse TREC data from CD4 and CD8 naïve and memory cell populations isolated from mouse splenocytes by FACS. CD4 Naïve=CD62L+, CD45RB+; CD4 Memory= CD62L–, CD45RB–. CD8 Naïve=CD62L+, CD45RB+; CD8 Memory=CD62L–, CD45RB–/dim. 100 molecules/ 100,000 cells is the lower limit of linear detection for this assay. Three sorting experiments have been performed with similar results.

FIGS. 2A and 2B: (FIG. 2A) Absolute number of thymocytes isolated from mice ranging in age from 6–90 weeks (n=3). Data are mean±SEM. (FIG. 2B) Molecules of mouse sjTRECs in thymocytes isolated from mice ranging in age from 6–90 weeks (n=3). Data are mean±SEM.

(FIG. 3A) Frequency of naïve phenotype CD4+ splenocytes in mice ranging in age from 6–90 weeks (n=3). Data are mean±SEM. (FIG. 3B) Frequency of naïve phenotype CD8+ splenocytes in mice ranging in age from 6–90 weeks (n=3). Data are mean±SEM. (FIG. 3C) Molecules of mouse sjTRECs in CD4+ splenocytes isolated from mice ranging in age from 6–90 weeks (n=3). Data are mean±SEM. (FIG. 3D) Molecules of mouse sjTRECs in CD8+ splenocytes isolated from mice ranging in age from 6–90 weeks (n=3). Data are mean±SEM.

DETAILED DESCRIPTION OF THE INVENTION

The present invention relates to a molecular assay (that includes primers, probe and standard) that can be used to detect and/or quantitate newly produced naïve T lymphocytes. The assay can be used to quantitate the level of thymopoiesis occurring in both in vivo and in vitro systems. The present assay makes possible rapid measurement of thymopoiesis in immune reconstitution strategies.

In accordance with the present invention, real-time quantitative-PCR can be used for the specific detection and quantification of mouse signal joint (sj) T cell receptor excision circles (TRECs). As indicated above, TRECs are episomal DNA circles that are generated by the DNA recombination process that is used by T lymphocytes to produce antigen-specific T cell receptors. As the non-replicated DNA circles are diluted out with cellular division, they represent molecular markers of newly generated naïve T lymphocytes. In the present assay, a cloned fragment of mouse TREC DNA serves as a quantitative standard (known number of molecules of TRECs).

PCR primers and labelled (e.g., fluorescent) probe for use in the invention are designed to span the mouse T cell receptor (TCR) delta excision circle signal joint. The signal joint sequence is unique and is present only in the circular TREC, it does not exist in genomic DNA. In practice, a fluorescently-labeled sequence-specific probe is quenched prior to cleavage by Taq DNA polymerase during PCR amplification. When amplification occurs, the probe is cleaved and the quencher is removed from the probe which then liberates fluorescence which can be detected using, for example, an ABI Prism 7700 system (Perkin-Elmer, Norwalk, Conn.). Fluorescent readings are, advantageously, taken at every PCR amplification cycle. ABI Prism Software can be used to determine the cycle number at which a given reaction crosses a fluorescence threshold (amplification above background). The lower the threshold cycle number, the more target template DNA in the sample.

Figure 1A:
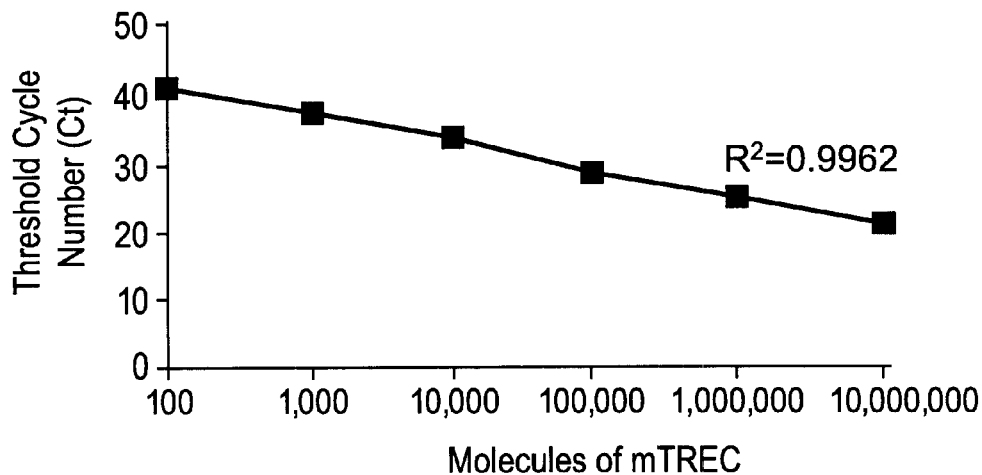
FIGS. 1A and 1B.

Genomic DNA from whole tissue, isolated cells, peripheral blood cells, MACS microbead separated cells (Miltenyi-Biotech, Auburn, Calif.), etc., can be amplified by real-time quantitative-PCR with the primers: CAT TGC CTT TGA ACC AAG CTG (SEQ ID NO:1) and TTA TGC ACA GGG TGC AGG TG (SEQ ID NO:2), and fluorescent probe FAM-CAG GGC AGG TTT TTG TAA AGG TGC TGC TCA CTT-QSY (SEQ ID NO:3). Alternatively, other primers (e.g., about 10 to about 25 bases long) can be used for the mouse TREC assay with the general characteristics of being downstream of the δRec and upstream of the pseudoJα of the mouse TCR α gene, and span the excised δRec/pseudoJα signal joint (Hockett et al, The New Biologist 1:266 (1989)). In a preferred embodiment, PCR reactions contain 0.5U Platinum taq polymerase (Gibco, Grand Island, N.Y.), 3.5 mM $MgCl_2$, 0.2 mM dNTPs, 500 nM each primer, 150 nM probe and Blue-636 reference dye (MegaBases, Evanston, Ill.). Amplification conditions are, advantageously, 95° C. for 5 minutes then 40 cycles of 95° C. for 30 seconds and 60° C. for 1 minute. Genomic DNA samples can be amplified and quantitated using an ABI Prism 7700 Sequence Detection System (Perkin Elmer). The mouse sjTREC sequence is cloned into a plasmid and used to generate a mouse TREC standard curve (FIG. 1A).

As indicated above, the present assay can be used to quantitate the level of thymopoiesis occurring in both in vivo and in vitro mouse systems. This assay provides a means for rapidly measuring thymopoiesis in immune reconstitution strategies. The present assay can be used to address the mechanics of acute and age induced thymic atrophy. Further the assay can be used to investigate T lymphocyte reconstitution strategies in preclinical studies in models (e.g., mouse models) of bone marrow transplantation.

The present invention relates not only to the assay described above but to kits suitable for use in such an assay. Kits of the invention can comprise one or more of the system components (primers, probe and standard), advantageously, disposed within one or more container means. The present kits can also include ancillary reagents (e.g., buffers) for use in carrying out the present assay.

Certain aspects of the invention can be described in greater detail in the non-limiting Example that follows.

EXAMPLE

Figure 1B:
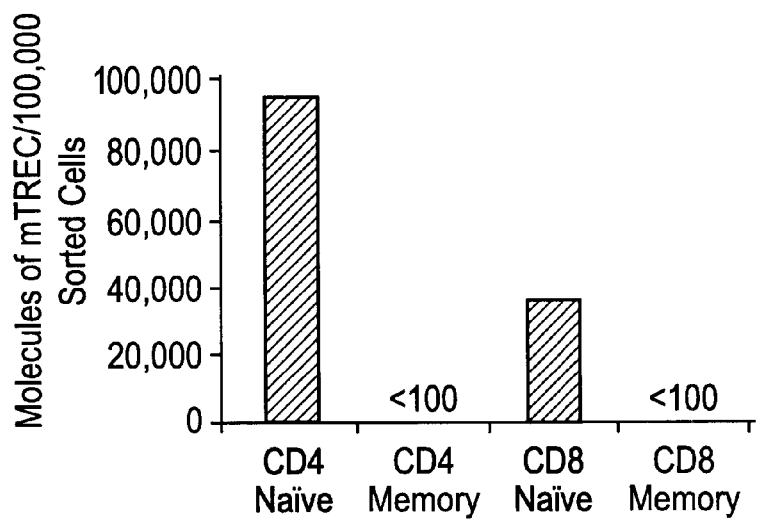

To validate the present assay for mouse TRECs three-color FACS was used to sort CD4+ and CD8+ naïve and memory cells. The number of molecules of TREC/100,000 cells analyzed is shown in FIG. 1B. The results demonstrated that the mouse TRECs detected with this assay were in the naïve T cell compartment.

The mouse TREC assay was next applied to address the question of thymic output in aging mice. First, the absolute number of thymocytes and the number of molecules of TRECs/100,000 thymocytes in a series of aged mice (range 6–90 weeks old) were examined (FIG. 2). It was found that the absolute number of thymocytes dramatically decreased with age and that molecules of TREC per 100,000 thymocytes also declined with mouse age, thus demonstrating a decrease in thymopoiesis in aged mice.

Figure 3A:
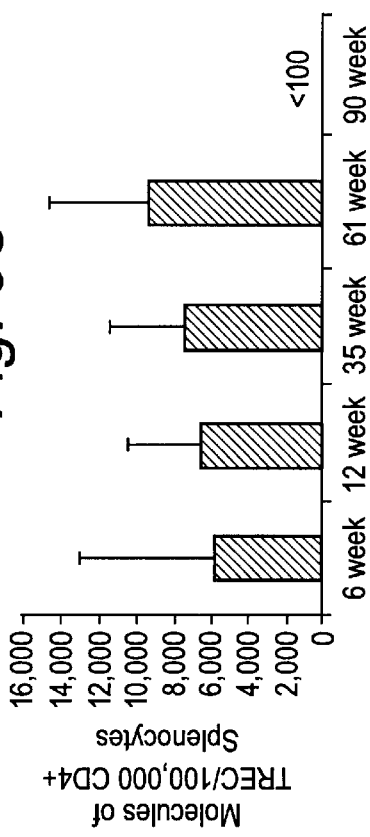
FIGS. 3A–3D.
Figure 3B:
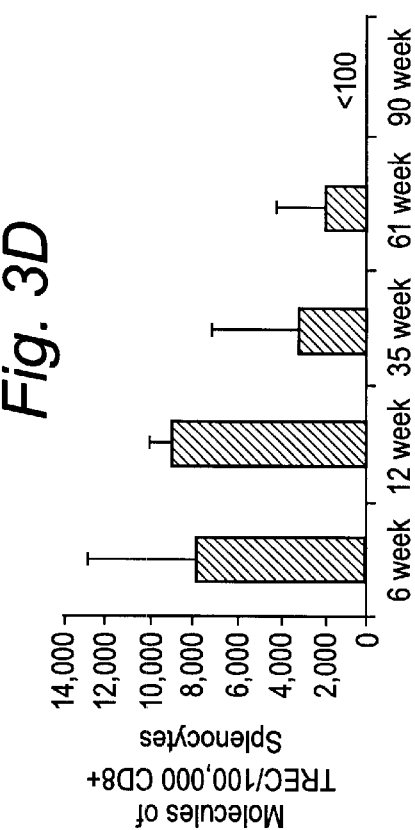
Figure 3C:
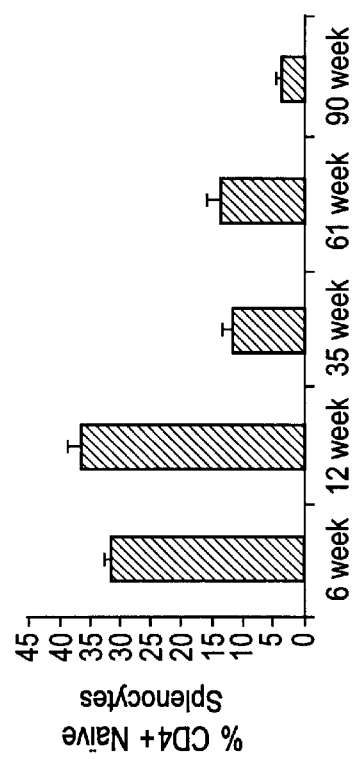
Figure 3D:
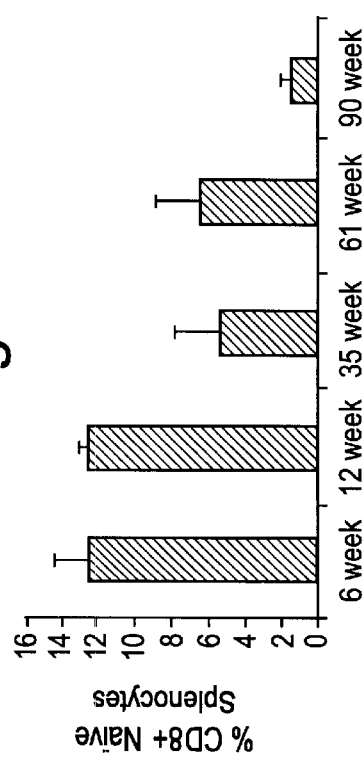

Second, the periphery of this cohort of aged mice was examined. Splenocytes were isolated from the animals and phenotyped by immunofluorescence and low cytometry (Naïve=CD62L+, CD45RB) to determine the frequency of naïve CD4 and CD8 cells present in these aged animals (FIGS. 3A and 3B). There was a drop in both CD4 and CD8 naïve peripheral T cells in the aged mice. Next, CD4+ and CD8+ splenocytes were purified from these samples (Miltenyi Beads) and, using the present real-time quantitative PCR assay for mouse TRECS, it was possible to determine the level of TRECs per 100,000 CD4+ and CD8+ splenocytes (FIGS. 3C and 3D). Interestingly, a constant level of TRECs was observed in the CD4 compartment until age 90 weeks. At this age, the number of TRECs in CD4+ cells dropped to below detection in the present assay. These data indicate that despite decreasing thymic output, the CD4 compartment maintains, to at least 61 weeks of age, a constant level of TREC+ cells. However, the data from CD8+ cells demonstrate a steady decline in TRECs/100,000 CD8+ splenocytes with increasing age, thus suggesting that mechanisms that prolong TREC+ cell half-life in the murine peripheral CD4 compartment are not at play in the peripheral CD8 compartment.

All documents cited above are hereby incorporated in their entirety by reference.

What is claimed is:

1. A method of detecting and quantitating mouse T cell receptor delta excision circles (TRECS) comprising:

i) contacting a genomic DNA sample with a pair of PCR primers that span the mouse pseudoJα/δRec T cell receptor delta signal joint and a labelled probe complementary to a region of said TRECs between the regions to which said primers hybridize, wherein said contacting is effected under conditions such that hybridization and amplification can occur, and ii) detecting and quantitating the amount of dissociated labelled probe resulting from said amplification, the amount of said dissociated probe being indicative of the amount of said TRECs present in said sample.

2. The method according to claim 1 wherein one of said primers comprises the sequence CAT TGC CTT TGA ACC AAG CTG (SEQ ID NO:1) and the other of said primers comprises the sequence TTA TGC ACA GGG TGC AGG TG (SEQ ID NO:2).

3. The method according to claim 1 wherein said probe is fluorescently labelled.

4. The method according to claim 3 wherein said probe comprises the sequence FAM CAG GGC AGG TTT TTG TAA AGG TGC TGC TCA CTT-QSY (SEQ ID NO:3).

5. A method of quantitating the level of thymopoiesis in a mouse comprising preparing a genomic DNA sample from said mouse and quantitating the number of TRECs present in said sample according to the method of claim 1.

6. The method according to claim 5 wherein said genomic DNA sample is prepared from the thymus of said mouse.

7. A method of monitoring immune reconstitution in a mouse comprising preparing a genomic DNA sample from said mouse and determining the number of TRECs present in said sample according to the method of claim 1.

8. The method according to claim 7 wherein said genomic DNA sample is prepared from the thymus of said mouse.

* * * * *